(12) United States Patent
Hirota et al.

(10) Patent No.: US 8,041,001 B2
(45) Date of Patent: Oct. 18, 2011

(54) IMAGE DIAGNOSING APPARATUS AND IMAGE DIAGNOSING METHOD

(75) Inventors: Shin Hirota, Tokyo (JP); Takayoshi Kurachi, Tokyo (JP); Yoshihiro Oda, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 1070 days.

(21) Appl. No.: 11/854,349

(22) Filed: Sep. 12, 2007

(65) Prior Publication Data

US 2008/0183475 A1    Jul. 31, 2008

(30) Foreign Application Priority Data

Sep. 14, 2006   (JP) ................. 2006-250027

(51) Int. Cl.
*H05G 1/10* (2006.01)
*H05G 1/60* (2006.01)
*A61B 5/05* (2006.01)

(52) U.S. Cl. ................. 378/8; 378/95; 600/407

(58) Field of Classification Search ............... 378/8, 95; 600/400–480; 704/270–278
See application file for complete search history.

(56) References Cited

U.S. PATENT DOCUMENTS

| | | | | |
|---|---|---|---|---|
| 4,878,499 | A | * 11/1989 | Suzuki et al. | 600/410 |
| 5,708,359 | A | 1/1998 | Gregory et al. | |
| 6,801,800 | B2 | * 10/2004 | Miyazaki et al. | 600/410 |
| 6,951,541 | B2 | 10/2005 | Desmarais | |
| 2003/0188757 | A1 | * 10/2003 | Yanof et al. | 128/916 |

FOREIGN PATENT DOCUMENTS

| | | | |
|---|---|---|---|
| JP | 05-056959 | 3/1993 | |
| JP | 05269125 | * 10/1993 | 378/1 |
| JP | 2002-165775 | 6/2002 | |
| JP | 2006-141906 | 6/2006 | |

* cited by examiner

*Primary Examiner* — Samuel G Neway
(74) *Attorney, Agent, or Firm* — Armstrong Teasdale LLP

(57) ABSTRACT

With the object of enabling a subject to be imaged at an appropriate timing of shooting, an image diagnosing apparatus for shooting an image of the subject in an imaging space has a voice guidance unit which reproduces and outputs to the subject a prescribed voice guidance and a voice output control unit which causes the output timing of the voice guidance outputted from the voice guidance unit to correspond with the timing of shooting the image of the subject.

16 Claims, 4 Drawing Sheets

IMAGE DIAGNOSING APPARATUS AND IMAGE DIAGNOSING METHOD

CROSS REFERENCE TO RELATED APPLICATIONS

This application claims the benefit of Japanese Application No. 2006-250027 filed Sep. 14, 2006.

BACKGROUND OF THE INVENTION

The present invention relates to image diagnosing apparatuses including radiographic apparatuses such as X-ray photographic apparatuses and X-ray CT (computed tomography) apparatuses and magnetic resonance imaging (MRI) apparatuses. It also relates to an image diagnosing method using such an image diagnosing apparatus.

An X-ray photographic apparatus, which takes X-ray photographs, is a type of non-destructive visual examination device which irradiates a subject with X-rays and visualizes the image shot mainly by printing it on a film to make the internal state of the subject known. And X-ray photographic apparatuses are put to practical use mainly in the field of medical care.

And in an X-ray CT apparatus, its scanning unit irradiates a subject with an X-ray beam while rotating an X-ray source around the subject, moves the subject in the direction of its body axis along with the rotation, and scans the volume of subject. Then, it generates images of sections of the subject on the basis of the data derived by the scanning. X-ray CT apparatuses are used for a wide range of purposes including medical uses and industrial uses.

Image diagnosing apparatuses, such as magnetic resonance imaging apparatuses, are known as apparatuses for shooting slice images of sections of a subject, and are used for a wide range of purposes including medical uses and industrial uses.

For instance, when a slice image is to be shot by using a magnetic resonance imaging apparatus, first a subject is accommodated in a space where a magnetostatic field is formed, and the spinning direction of protons in the subject, which is a living organism, is aligned with the direction of the magnetostatic field to achieve a state in which a magnetization vector is obtained. After that, the magnetization vector of the protons of the subject is varied by irradiating the subject with an electromagnetic wave of the resonance frequency from an RF coil and thereby generating a nuclear magnetic resonance phenomenon. And the magnetic resonance imaging apparatus receives with the RF coil magnetic resonance signals from the protons of the subject returning to the original magnetization vector, and generates a slice image on the basis of the received magnetic resonance signals (see Patent Document 1 for instance).

Every one of the image diagnosing apparatuses described above as examples including X-ray photographic apparatuses, X-ray CT apparatuses and magnetic resonance imaging apparatuses shoots images of the subject in an imaging space. The imaging space in this context means a prescribed area of the subject where X-rays irradiating the subject are transmitted in an X-ray photographic apparatus. In an X-ray CT apparatus, the imaging space means a prescribed area of the subject in which the scanning unit of the X-ray CT apparatus irradiates the subject with an X-ray beam while rotating the beam source around the subject and shifts in the direction of the body axis of the subject along with the rotation. In the magnetic resonance imaging apparatus, the imaging space means a prescribed area of the subject in which a slice image is generated on the basis of magnetic resonance signals received by the RF coil.

When an image of a subject is to be shot by using an image diagnosing apparatus, as the subject is always being moved by respiration or otherwise, the shot image may be blurred or suffer the generation of artifacts. Therefore, when taking an image of a subject with an image diagnosing apparatus, the operator tells the subject "Halt breathing" or "Inhale and then halt breathing". Then, the subject temporarily halts his or her bodily motion by halting respiration in accordance with the operator's instruction, and the image is shot at the right timing.

Further, the image diagnosing apparatus may be provided with an auto-voice function to automatically issue a breathing halt instruction, such as "Halt breathing" or "Inhale and then halt breathing", before shooting an image of the subject and to shoot after that instruction (vocal) thereby to catch the right timing of shooting. To further ensure the right timing of shooting, some X-ray CT apparatus, such as the one described in Patent Document 2, is provided with a respiration sensor which detects the subject's respiration either directly or indirectly, and shoots an image after the respiration sensor detects breathing halt after the breathing halt has been instructed.

[Patent Document 1] Japanese Unexamined Patent Publication No. 2002-165775
[Patent Document 2] Japanese Unexamined Patent Publication No. Hei 05 (1993)-056959

As the subject is enabled to halt his or her respiration in accordance with the breathing halt instruction by equipping an image diagnosing apparatus with an auto-voice function or having its operator giving an instruction directly to the subject, image shooting can be accomplished at the right timing.

Equipping the image diagnosing apparatus with an auto-voice function to give instructions to the subject uniformly determines the voice reproduction speed of the auto-voice function. Thus, the length of time from the start until the end of a voice message of the auto-voice function is fixed.

On the other hand, the timing of image shooting is not necessarily determined uniformly. For instance, when a contrast medium is administered to the subject before image shooting, there is a time lag until the administered contrast medium reaches the imaging space and the right timing of image shooting comes. And this time lag may vary in many ways with the positions of the subject or of the imaging space.

For this reason, the time lag and the length of time from the start until the end of the voice message may offer differ from each other, and even when the subject halts his or her respiration as instructed by the voice message, a lag may occur between the timing of the breathing halt and the timing of image shooting.

Furthermore, even if the length of time from the start until the end of the voice message of the auto-voice function is fixed, the subject may not be always able to halt his or her respiration exactly in accordance with the voice message. For instance, in response to the voice message "Inhale and then halt breathing", some subject may hurriedly inhale and halt breathing while another may slowly inhale a long breadth and halt breathing. This would also invite a lag between the timing of breathing halt and the timing of image shooting. Especially where the subject is high-aged, his or her reaction to the reproducing speed of the voice message may be delayed, often making it difficult to respire in accordance with the voice message.

SUMMARY OF THE INVENTION

It is desired that the problems heretofore described are solved.

According to one aspect of the invention, there is provided an image diagnosing apparatus for shooting an image of a subject in an imaging space, which has a voice guidance unit which reproduces and outputs to the subject a prescribed voice guidance; and a voice output control unit which exercises such control over the voice guidance unit as causes the output timing of the voice guidance outputted from the voice guidance unit to correspond with the timing of shooting the image of the subject.

Preferably, the voice output control unit should cause the output timing of the voice guidance outputted from the voice guidance unit to correspond with the timing of shooting the image of the subject by so controlling the voice guidance unit as to match the starting time of shooting the subject with the time at which reproduction and outputting of the voice guidance end.

More specifically, the voice output control unit exercises control over the voice guidance unit to cause the output timing of the voice guidance to correspond with the timing of shooting the image of the subject by varying the reproducing speed of the voice guidance.

Further, the voice output control unit exercises control over the voice guidance unit to cause the timing of breathing halt of the subject as the timing of shooting the image of the subject to correspond with the output timing of the voice guidance.

Incidentally, the respiration timing of the subject is a timing of sequentially performing one or more of inhalation, exhalation and breathing halt, and the voice output control unit exercises control over the voice guidance unit to cause the time at which reproduction and outputting of the voice guidance start to correspond with the timing of inhalation by the subject and the time at which reproduction of the voice guidance ends to correspond with the timing of breathing halt by the subject.

Preferably, the content of the voice guidance should be to sequentially notify the subject of one or more of the effects of "inhalation", "exhalation" and "breathing halt", and the voice output control unit should exercise control over the voice guidance unit to cause the time at which the effect of "inhalation" of the voice guidance is reproduced with the timing of inhalation by the subject, to cause the time at which the effect of "exhalation" is reproduced with the timing of exhalation by the subject, and to cause the time at which the effect of "breathing halt" is reproduced with the timing of breathing halt by the subject.

More preferably, the apparatus should further have a respiration sensor for measuring the respiration timing of the subject, the respiration sensor notifying the voice output control unit of the measured respiration timing of the subject, and the voice output control unit exercising control over the voice guidance unit to have the reproducing speed of the voice guidance varied.

Incidentally, the data of the voice guidance comprise a plurality of kinds of data classified by the pattern of the output timing of the voice guidance, and the voice output control unit exercises control over the voice guidance unit to cause the output timing of the voice guidance outputted from the voice guidance unit to correspond with the timing of shooting the image of the subject by using one kind of the classified plurality of kinds of data matched with the timing of shooting the image of the subject.

Or else, the data of the voice guidance may comprise one kind of data, the voice output control unit exercising control over the voice guidance unit to cause the output timing of the voice guidance outputted from the voice guidance unit to correspond with the timing of shooting the image of the subject by exercising control to adjust the speed of reproducing and outputting the one kind of data to the voice guidance unit.

Suitably, the apparatus should further have an input unit which allows inputting of the speed of reproduction and outputting to the voice guidance unit.

According to another aspect of the invention, there is also provided an image diagnosing method of shooting an image of a subject in an imaging space with an image diagnosing apparatus having a voice guidance unit which reproduces and outputs to the subject a prescribed voice guidance, wherein the output timing of the voice guidance outputted from the voice guidance unit is caused to correspond with the timing of shooting the image of the subject.

Preferably, the output timing of the voice guidance outputted from the voice guidance unit should be caused to correspond with the timing of shooting the image of the subject by matching the time at which the shooting of the subject starts with the time at which the reproduction and outputting of the voice guidance end.

More specifically, the output timing of the voice guidance is caused to correspond with the timing of shooting the image of the subject by varying the reproducing speed of the voice guidance.

Further, the timing of breathing halt of the subject is caused to correspond with the output timing of the voice guidance as the timing of shooting the image of the subject.

Incidentally, the respiration timing of the subject is the timing of one or more in the sequential performance of inhalation, exhalation and breathing halt, the time at which reproduction and outputting of the voice guidance start is caused to correspond with the timing of inhalation by the subject, and the time at which reproduction and outputting of the voice guidance end is caused to correspond with the timing of breathing halt by the subject.

Preferably, the content of the voice guidance should be to sequentially notify the subject of one or more of the effects of "inhalation", "exhalation" and "breathing halt", the time at which the effect of "inhalation" of the voice guidance is reproduced being caused to correspond with the timing of inhalation by the subject, the time at which the effect of "exhalation" is reproduced being caused to correspond with the timing of exhalation by the subject, and the time at which the effect of "breathing halt" is reproduced ends being caused to correspond with the timing of breathing halt by the subject.

The image diagnosing apparatus and the image diagnosing method according to the present invention enables a subject to be imaged at the right timing of shooting.

Further objects and advantages of the present invention will be apparent from the following description of the preferred embodiments of the invention as illustrated in the accompanying drawings.

DETAILED DESCRIPTION OF THE INVENTION

Figure 1:
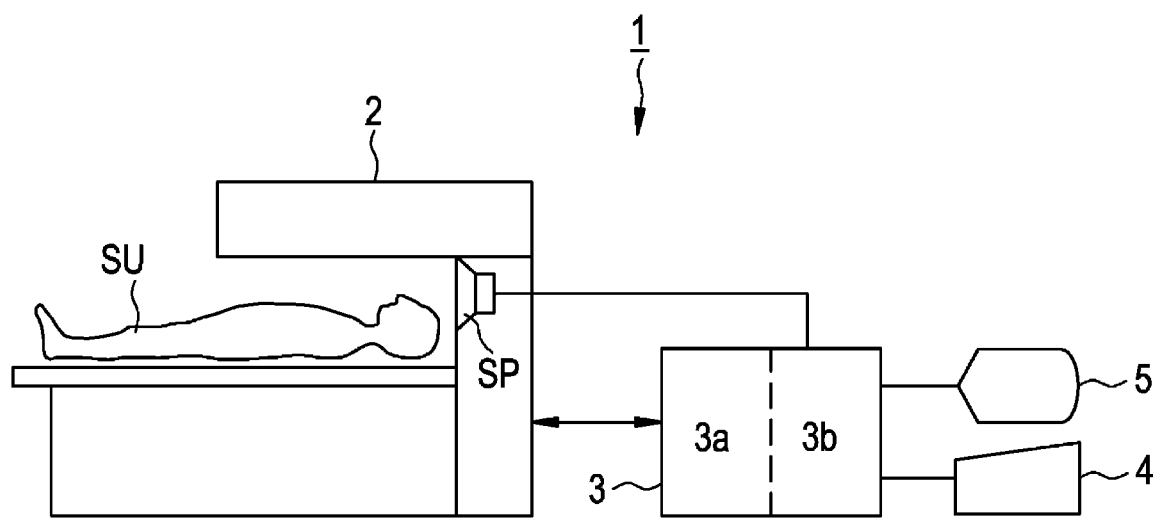
FIG. 1 is a block diagram showing the overall configuration of an image diagnosing apparatus in a mode for carrying out the present invention.

FIG. 1 is a block diagram showing the overall configuration of an image diagnosing apparatus 1 pertaining to the present invention.

As shown in FIG. 1, the image diagnosing apparatus 1 has a diagnosing apparatus body 2, a control unit 3, an input unit 4, a display unit 5 and a voice guidance unit SP.

Where the image diagnosing apparatus 1 is an X-ray CT apparatus, the diagnosing apparatus body 2 has an X-ray tube, an X-ray tube shifting unit, a collimator, an X-ray detector, a data collecting unit, an X-ray controller, a collimator controller, a rotating unit, a gantry controller and a subject carrying unit.

In the diagnosing apparatus body 2, the subject carrying unit shifts the table in the imaging space, a subject SU supported by that table is scanned with X-rays, and projected from that subject SU are obtained as raw data. For instance, the diagnosing apparatus body 2 helically scans a prescribed area of the subject SU into which a contrast medium has been injected. The control of helical scanning by the diagnosing apparatus body 2 is accomplished by the control unit 3 described below. Incidentally, the diagnosing apparatus body 2 in this case is the diagnosing apparatus body of a usual X-ray CT apparatus, and details of the operation referred to above are described in, for instance, Japanese Unexamined Patent Publication No. 2006-141906.

Where the image diagnosing apparatus 1 is a magnetic resonance imaging apparatus, the diagnosing apparatus body 2 has a table on which the subject SU is mounted and a gantry in which a magnet for applying a magnetic field to the subject SU is stored. In shooting an image of the subject with the diagnosing apparatus body 2, the control unit 3 described below performs control to apply a gradient magnetic field to a gradient coil in the gantry in the slice selecting direction of the subject and control to have the RF coil in the gantry irradiate the subject with an electromagnetic wave of the resonance frequency and receive resonance magnetic signals from protons in the subject SU. Incidentally, the diagnosing apparatus body 2 in this case is the diagnosing apparatus body of a magnetic resonance imaging apparatus, and as its configuration is well known to persons in the skilled in the art, detailed description is dispensed with here.

The image diagnosing apparatus 1 shown in FIG. 1 has an imaging space, and shoots an image of the subject SU mounted on the table of the diagnosing apparatus body 2. Where the image diagnosing apparatus 1 is an X-ray CT apparatus, the imaging space is a prescribed area corresponding to the range in which the scanning unit of the X-ray CT apparatus irradiates the subject with an X-ray beam while rotating the X-ray source around the subject and the subject is shifted in the direction of its body axis along with that rotation. And where the image diagnosing apparatus 1 is a magnetic resonance imaging apparatus, the imaging space is a prescribed area of the subject SU in which a slice image is generated on the basis of magnetic resonance signal received by an RF coil.

The control unit 3 comprises a control unit 3a for exercising prescribed control over the diagnosing apparatus body 2 to image the subject SU mounted on the diagnosing apparatus body 2, and a voice output control unit 3b for exercising control over the voice guidance unit SP to have a prescribed voice guidance reproduced and outputted. Although the configuration of the control unit 3 is partitioned into the control unit 3a and the voice output control unit 3b in FIG. 1 for the convenience of description, they may as well be configured of an integrated electronic computer. The electronic computer, like a usual electronic computer, would have a central processing unit and a memory unit, and be cause to perform the following control, encoding and other information processing actions.

The control unit 3a, where the image diagnosing apparatus 1 is an X-ray CT apparatus, shifts the subject SU mounted on the table of the diagnosing apparatus body 2 by having it carried to the imaging space. And the control unit 3a outputs a control signal to the gantry controller to rotate the rotating unit of the scanning gantry. And the control unit 3a outputs a control signal to the X-ray controller so as to radiate X-rays from the X-ray tube. And the control unit 3a outputs a control signal to the collimator controller to control the collimator to shape the X-rays. Also, the control unit 3a so controls data collecting unit as to collect projected data obtained by the detection element of the X-ray detector.

The control unit 3a, where the image diagnosing apparatus 1 is a magnetic resonance imaging apparatus, delivers to the diagnosing apparatus body 2 control data regarding application of a gradient magnetic field to the gradient coil in the gantry in the slice selecting direction of the subject and irradiation of the subject with an electromagnetic wave of the resonance frequency by the RF coil in the gantry. And the diagnosing apparatus body 2 delivers to the control unit 3a reception data of resonance magnetic signals from protons in the subject.

The input unit 4 is configured of input devices such as a keyboard and a mouse. And when the control unit 3a is to designate the region of the subject SU to be imaged or when requires the inputting of other data, inputting to the input unit 4 is performed, and the inputted data are delivered to the control unit 3.

The display unit 5 is configured of a display device such as a liquid crystal display. Where the image diagnosing apparatus 1 is an X-ray CT apparatus, the display unit 5 displays the image of a section of the subject SU resulting from reconstruction by the control unit 3a of projected data collected by the data collecting unit. Where the image diagnosing apparatus 1 is a magnetic resonance imaging apparatus, the slice image of the subject obtained by the control unit 3a by encoding resonance magnetic signals received by the RF coil is displayed. Also, the display unit 5 displays information regarding the manipulation of the input unit 4 required by the operator in manipulating the image diagnosing apparatus 1.

A case of imaging the subject SU by using the image diagnosing apparatus 1 having the configuration described above as shown in FIG. 1 will be described with reference to FIG. 2.

FIG. 2 are time charts for automatically issuing, in the image diagnosing apparatus 1 shown in FIG. 1 before shooting the subject SU, a voice guidance from the voice guidance unit SP consisting of a message to the effect of instructing a breathing halt such as "Halt breathing" or "Inhale and then halt breathing" under the control of the voice output control unit 3b, and performing the shooting immediately after the end of that voice guidance.

It is further supposed in FIG. 2 that a contrast agent is injected into the subject SU and shooting is started at the time when the injected contrast medium has reached the imaging space (point) of the subject SU as the suitable timing for shooting. And that the subject SU has halted his or her respiration in accordance with the voice guidance at the time the injected contrast medium has reached the imaging space (point) of the subject SU constitutes the condition of ensuring that the shot image is free from blurring or artifacts.

Figure 2A:
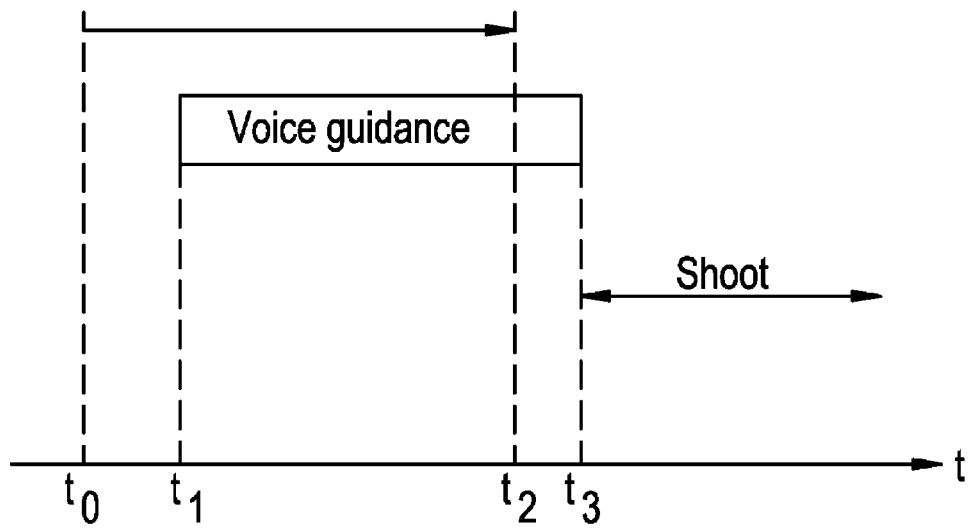
FIGS. 2(a) and 2(b) are time charts regarding cases in which a subject is imaged by using the image diagnosing apparatus.

FIG. 2(a) shows a case in which the control of reproduction and outputting of the voice guidance from the voice guidance unit SP is not appropriately accomplished by the voice output control unit 3b. This will be described in a time series. First at a point of time t0, the contrast medium is injected into the subject SU. A prescribed length of time is required until the contrast medium reaches the imaging space (point) of the subject SU and when a point of time t2 has come, the contrast medium reaches the imaging space (point) of the subject SU.

After the contrast medium is injected into the subject SU at point of time t0, the reproduction and outputting of the voice guidance from the voice guidance unit SP consisting of a message to the effect of instructing a breathing halt such as "Halt breathing" or "Inhale and then halt breathing" are started at a point of time t1. A prescribed length of time is required from this start of the voice guidance until its end, and when a point of time t3 has come, the reproduction and outputting of the voice guidance end, immediately followed by the start of shooting.

However, if the control of reproduction and outputting of the voice guidance from the voice guidance unit SP is not appropriately accomplished by the voice output control unit 3b, the point of time t2 at which the contrast medium reaches the imaging space (point) of the subject SU may come earlier than the point of time t3 at which the reproduction and outputting of the voice guidance end as shown in FIG. 2(a). Then, as the subject SU halts breathing after the contrast medium has reached the imaging space (point) of the subject SU, the timing of shooting will become inappropriate.

Figure 2B:
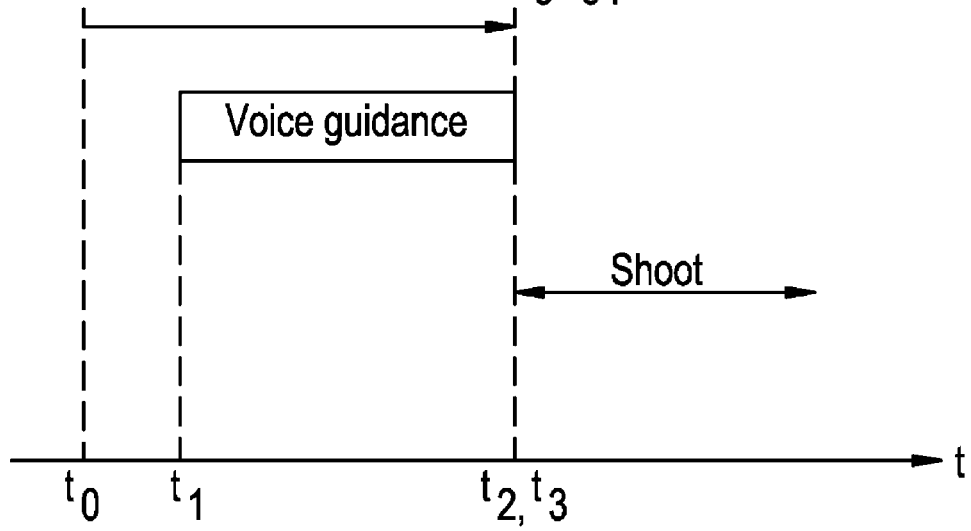

Therefore, it is necessary to cause the output timing of the voice guidance outputted from the voice guidance unit SP to correspond with the timing of shooting the image of the subject SU. More specifically, it is necessary to cause the time of start imaging the subject SU to correspond with the time at which the reproduction and outputting of the voice guidance by the voice guidance unit SP end. FIG. 2(b) shows an example of this necessity. In FIG. 2(b), the reproducing speed of the reproduction and outputting of the voice guidance consisting of a message to the effect of instructing a breathing halt such as "Halt breathing" or "Inhale and then halt breathing" shown in FIG. 2(a) is varied. More specifically, according to FIG. 2(b), control to make the reproducing speed of the voice guidance faster than in FIG. 2(a) is performed by the voice output control unit 3b on the voice guidance unit SP.

The setting of the reproducing speed of the voice guidance can be accomplished by the operator of the image diagnosing apparatus 1 by so performing an operation to make an input to the input unit 4 as to accelerate the reproducing magnification of the reproducing speed of the voice guidance. Thus, when injecting the contrast medium into the subject SU, though the length of time taken by the contrast medium after its injection into the subject SU to reach the imaging space (point) differs with the type and quantity of the contrast medium, they are already roughly known from past imaging records, and therefore the operator can set the reproducing magnification by rule of thumb.

Or else, the operator's inputting of the length of time taken after the injection until into the subject SU to reach the imaging space (point) to the input unit 4 can also cause the electronic computer of the voice output control unit 3b to compute the reproducing speed of the voice guidance.

The case in which the reproducing magnification of the reproducing speed of the voice guidance has been appropriately set will be described with reference to the time chart of FIG. 2(b).

First at the point of time t0, the contrast medium is injected into the subject SU. A prescribed length of time is required by the contrast medium to reach the imaging space (point) and, when the point of time t2 has come, the contrast medium reaches the imaging space (point) of the subject SU.

After the contrast medium is injected into the subject SU at the point of time t0, the reproduction and outputting of the voice guidance consisting of a message to the effect of instructing a breathing halt such as "Halt breathing" or "Inhale and then halt breathing" from the voice guidance unit SP are started at the point of time t1. And when the point of time t3 has come, the reproduction and outputting of the voice guidance end, and shooting starts immediately after that.

Since the reproducing magnification of the reproducing speed of the voice guidance is appropriately set as shown in FIG. 2(b), the point of time t2 at which the contrast medium reaches the imaging space (point) of the subject SU corresponds with the point of time t3 when the reproduction and outputting of the voice guidance end. This puts an end to the reproduction and outputting of the voice guidance, and the point of time when the subject SU completes his or her breathing halt and the starting time of shooting the subject SU correspond with each other. Therefore, the timing of shooting the subject SU is appropriately set.

Another case of shooting the subject SU by using the image diagnosing apparatus 1 shown in FIG. 1 will be described with reference to FIG. 3.

FIG. 3 are time charts for automatically issuing, in the image diagnosing apparatus 1 shown in FIG. 1 before shooting the subject SU, a voice guidance from the voice guidance unit SP consisting of messages "Exhale" to the effect of instructing "exhalation", "Inhale" to the effect of instructing "inhalation" and "Halt breathing" to the effect of breathing halt under the control of the voice output control unit 3b, and performing the shooting immediately after the end of that voice guidance.

Referring to the time charts shown in FIG. 3, the state in which the subject SU is holding his or her breath in accordance with the instruction of "Halt breathing" at the end of the voice guidance is the state suitable for shooting.

To ensure that, when the reproduction of the message "Inhale" from the voice guidance unit SP started at a point of time tIN on the time axis in the time charts of FIG. 3, it is necessary for the subject SU to have started inhalation. And if the reproduction of the message "Exhale" reproduced from the voice guidance unit SP is started the point of time tEX after the subject SU has started inhalation, it is necessary for the subject SU to have started exhalation. Finally, at the point of time tHA, at the time the reproduction of the message "Halt breathing" reproduced from the voice guidance unit SP has ended, it is necessary for the subject SU to have started breathing halt.

Figure 3A:
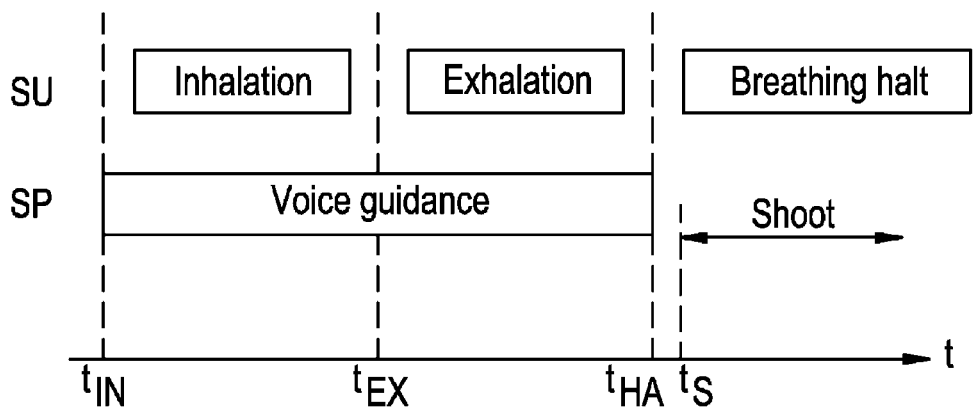
FIGS. 3(a), 3(b), and 3(c) are time charts regarding cases in which a subject is imaged by using the image diagnosing apparatus.

In the example shown in FIG. 3(a), the subject SU is inhaling from the point of time tIN toward the point of time tEX, exhaling from the point of time tEX toward the point of time tHA, and from the point of time tHA onward is not respiring. Since the subject SU is therefore holding his or her breath from the point of time tHA onward in accordance with the instruction of the voice guidance "Halt breathing", a suitable state for shooting comes at the point of time ts.

Here is considered, with reference to the time chart shown in FIG. 3(a), a case in which a message of the same reproducing speed as the message reproduced by the voice guidance unit SP is reproduced by the voice guidance unit SP and another subject SU', different from the subject SU in FIG. 3(a) is shot. The time chart of this shooting is shown in FIG. 3(b).

Figure 3B:
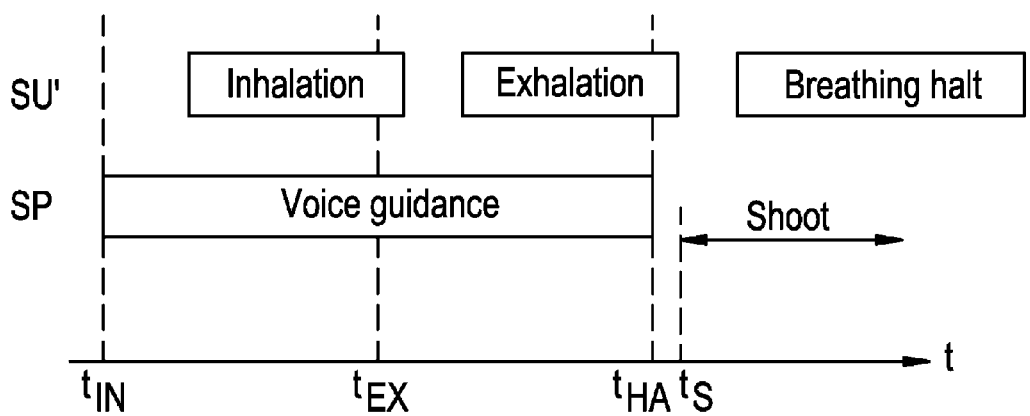

FIG. 3(b) supposes a case in which the subject SU' is high-aged for instance, and according it is difficult for him or her to inhale, exhale and halt breathing exactly following the messages "Exhale", "Inhale" and "Halt breathing".

In this case, though the reproduction of the message "Exhale" from the voice guidance unit SP was already started at the point of time tEX, the subject SU' is still inhaling and, though the reproduction of the message "Halt breathing" from the voice guidance unit SP already ended at the point of time tHA, the subject SU' is still exhaling.

Therefore, it is only after the point of time ts, when it is suitable for shooting, has passed that the subject SU' is holding his or her breath. As a result, since the subject SU' is still exhaling when shooting takes place at the point of time ts, a bodily motion of the subject SU' may occur to blur the shot image or let artifacts arise in it.

Then, it is necessary to cause the output timing of the voice guidance outputted from the voice guidance unit SP to correspond with the timing of shooting an image of the subject SU'. In this case, it is necessary to cause the time of starting image shooting of the subject SU to correspond with the time at which the reproduction and outputting of "Halt breathing" at the end of the voice guidance by the voice guidance unit SP end.

Figure 3C:
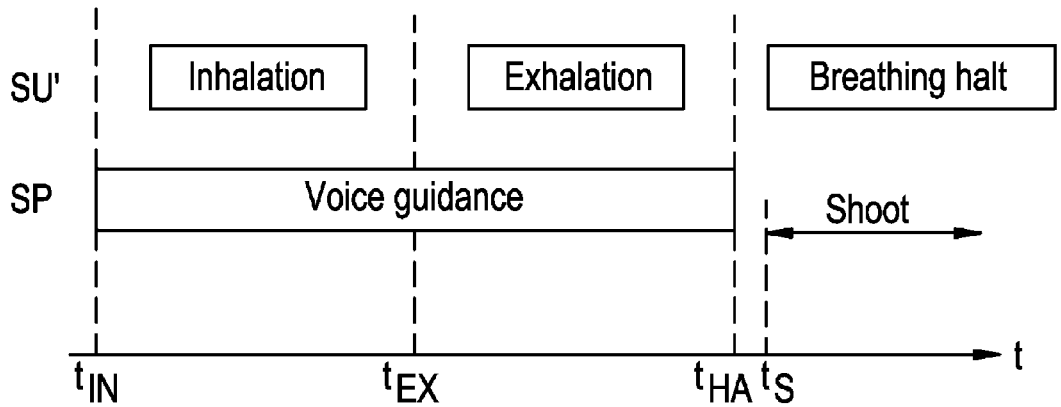

FIG. 3(c) shows an example of it. In FIG. 3(c), the reproducing speed of reproducing and outputting the voice guidance consisting of the sequence of messages "Exhale", "Inhale" and "Halt breathing" shown in FIG. 3(b) is varied.

More specifically, according to FIG. 3(c), the voice output control unit 3b exercises over the voice guidance unit SP such control as makes the reproducing speed of the voice guidance slower than in the case of FIG. 3(b). In order to make the reproducing speed of the voice guidance slower, for instance the operator can make an input to the input unit 4 as to decelerate the reproducing magnification of the reproducing speed of the voice guidance.

As the reproducing speed of the voice guidance in FIG. 3(c) is slower than in FIG. 3(b), the subject SU' inhales from the point of time tIN toward the point of time tEX, exhales from the point of time tEX toward the point of time tHA, and holds respiration from the point of time tHA onward. Thus, the subject SU' is in the state of inhaling, exhaling and holding respiration by exactly following the messages "Exhale", "Inhale" and "Halt breathing" reproduced from the voice guidance unit SP.

In this state, the voice output control unit 3b is exercising such control over the voice guidance unit SP as causes the time of starting reproduction and outputting of the voice guidance to correspond with the timing of inhalation and the time of ending reproduction of the voice guidance with the timing of halting breathing by the subject SU'.

Since the subject SU' is holding his or her breath from the point of time tHA onward in accordance with the instruction of "Halt breathing" at the end of the voice guidance, a suitable state for shoot comes at the point of time ts.

However, as the respiration of the subject SU' may be irregular, it may be sometimes difficult to enable the subject SU' to inhale exactly from the point of time tIN toward the point of time tEX merely by inputting the reproducing magnification of the reproducing speed of the voice guidance and slowing down the reproducing speed of the voice guidance by making an input to the input unit 4. Similarly, it may be difficult for the subject SU' to hold breathing exactly from the point of time tHA onward.

In view of this problem, the respiration timing of the subject SU' can be measured and control can be exercised by the voice output control unit 3b over the voice guidance unit SP to vary the reproducing speed of the voice guidance interlocked with that measured respiration timing.

Figure 4:
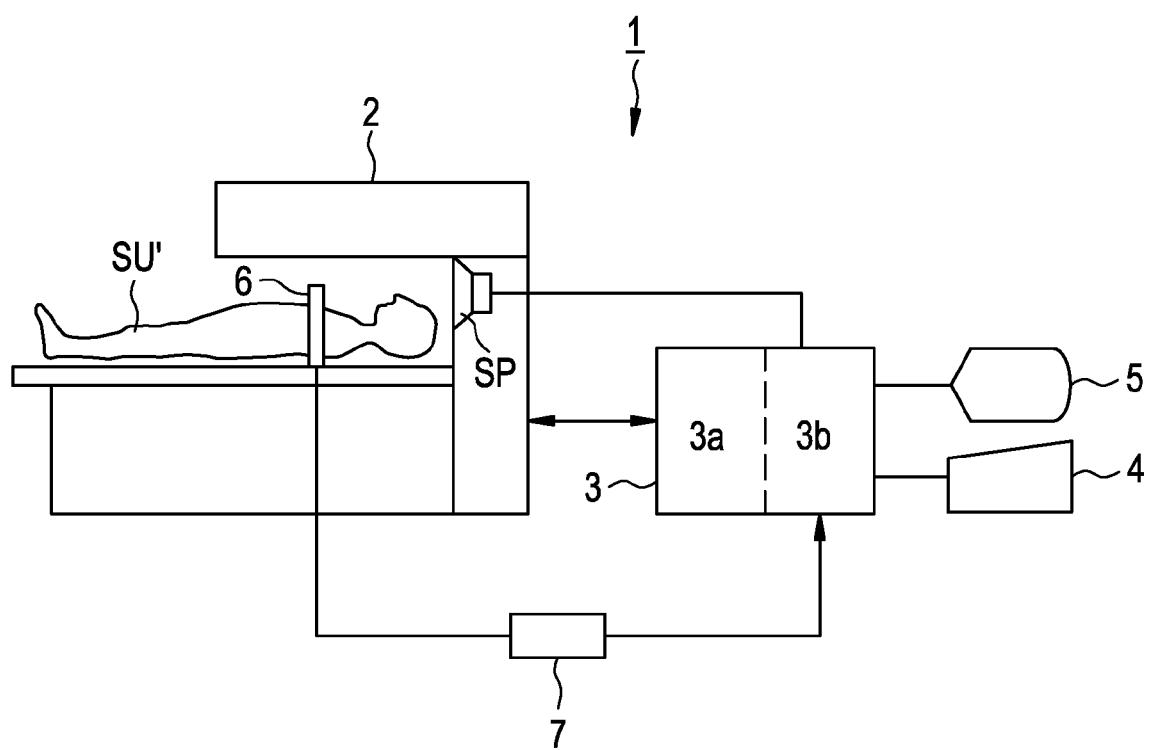
FIG. 4 is a block diagram showing the overall configuration of an image diagnosing apparatus in another mode for carrying out the invention.

The image diagnosing apparatus 1 shown in FIG. 4 is a version of the image diagnosing apparatus 1 shown in FIG. 1 with its diagnosing apparatus body 2 provided with a respiration sensor 6 for measuring the respiration timing of the subject SU. Elements of the diagnosing apparatus 1 shown in FIG. 4 that are the same as elements of the diagnosing apparatus 1 shown in FIG. 1 are designated using the same reference number. And the voice output control unit 3b is provided with a respiration waveform input device 7 which outputs to the voice output control unit 3b as the respiration waveform the respiration timing measured by the respiration sensor 6. A respiration sensor in normal medical use can be used as the respiration sensor 6, and the respiration waveform input device 7 can also be one normally used for such medical purposes.

A case of shooting an image of the subject SU' by using the image diagnosing apparatus 1 shown in FIG. 4 will be described with reference to the time chart shown in FIG. 3(c) regarding the case of shooting an image of the subject SU'.

As the respiration sensor 6 is fitted to the subject SU', when the subject SU' starts inhalation, the respiration sensor 6 detects it and delivers the detection signal to the respiration waveform input device 7. And the voice output control unit 3b receives it as a signal of the respiration waveform from the respiration waveform input device 7. Similarly, when the subject SU' starts exhalation, the respiration sensor 6 detects it and delivers the detection signal to the respiration waveform input device 7, and the voice output control unit 3b receives it as a signal of the respiration waveform from the respiration waveform input device 7.

Referring to FIG. 3(c), when the voice output control unit 3b has received a respiration waveform signal regarding the start of inhalation by the subject SU', it exercises such control over the voice guidance unit SP as to have the voice guidance unit SP reproduce the message "Inhale" at the point of time tIN.

And even during the reproduction of the message "Inhale", the voice output control unit 3b can predict with the electronic computer within the voice output control unit 3b the ending time of inhalation by the subject SU' from the respiration waveform signal. Then, the voice output control unit 3b exercises control over the voice guidance unit SP to so vary the reproducing speed as to cause the reproduction of the message "Inhale" to end by the ending time of inhalation.

Referring to FIG. 3(c), when the voice output control unit 3b has received a respiration waveform signal regarding the start of exhalation by the subject SU', it exercises such control over the voice guidance unit SP as to have the voice guidance unit SP reproduce the message "Exhale" at the point of time tEX.

And even during the reproduction of the message "Exhale", the voice output control unit 3b can predict from the respiration waveform signal with the electronic computer within the voice output control unit 3b the point of time tHA at which exhalation by the subject SU' ends and the breathing halt starts.

Then, the voice output control unit 3b exercises control over the voice guidance unit SP to so vary the reproducing speed as to cause the reproduction of the message "Exhale" to end by the ending time of exhalation and, after the end of reproduction of that message, to complete the start of reproduction and the end of reproduction of the message "Halt breathing" by the ending time of exhalation.

As described above, the respiration timing of the subject SU' is constantly performed, and the voice output control unit 3b exercises control over the voice guidance unit SP to vary the reproducing speed of the voice guidance interlocked with that measured respiration timing. In this way, since the subject SU' is holding his or her breath from the point of time tHA onward as shown in FIG. 3(c) in accordance with the instruction of "Halt breathing" at the end of the voice guidance, a suitable state for shooting is achieved at the point of time ts.

The control by the voice output control unit 3b to vary the reproducing speed of the message reproduced by the voice guidance unit SP as described above is jointly accomplished by the central processing unit and the memory unit of the electronic computer within the voice output control unit 3b.

Incidentally, as data of the messages outputted from the voice guidance unit SP and varied in reproducing speed, data stored in the memory unit for each of various reproducing speed patterns can be used for each message. In this case, a vast quantity of data on messages for all conceivable reproducing speeds should be stored in the memory unit.

However, where the voice output control unit 3b is to reproduce a given message at a prescribed speed out of the voice guidance unit SP, as it is sufficient to read out of the memory unit one set of data to whose speed the central processing unit is adaptable and to output the data to the voice guidance unit SP, there is less load on the central processing unit.

On the other hand, only one kind of data regarding each of the messages stored in the memory unit can be used as data of the messages outputted from the voice guidance unit SP and varied in reproducing speed. In this way, the load the memory unit can be reduced.

However, since there is only one kind of data for each message, when the reproducing speed of any message is to be varied, the central processing unit of the voice output control unit 3b has to read the pertinent data out of the memory unit, and re-encode the data to match the reproducing speed. For this reason, the load on the central processing unit may increase.

Regarding the data of messages outputted from the voice guidance unit SP and varied in reproducing speed, it is of course freely selectable whether to use data stored in the memory unit for each of various reproducing speed patterns or only one kind of data for each message.

FIG. 3 charted reproduction from the voice guidance unit SP under the control of the voice output control unit 3b a total of three kinds of messages "Exhale" to the effect of instructing "exhalation", "Inhale" to the effect of instructing "inhalation" and "Halt breathing" to the effect of breathing halt. However, it is not necessary to use all these three kinds of messages. It is also conceivable to have the voice guidance unit SP sequentially reproduce only two kinds of messages including "Inhale" to the effect of instructing "inhalation" and "Halt breathing" to the effect of breathing halt.

Many widely different embodiments of the invention may be configured without departing from the spirit and the scope of the present invention. It should be understood that the present invention is not limited to the specific embodiments described in the specification, except as defined in the appended claims.

The invention claimed is:

1. An image diagnosing apparatus for shooting an image of a subject in an imaging space, the image diagnosing apparatus comprising:
   a voice guidance unit which reproduces and outputs to said subject a prescribed voice guidance; and
   a voice output control unit which exercises control over said voice guidance unit to cause an output timing of the voice guidance outputted from said voice guidance unit to correspond with the timing of shooting the image of said subject, wherein said voice output control unit is configured to predict at least one of an ending time of inhalation by said subject and an ending time of exhalation by said subject, said voice output control unit exercises control over said voice guidance unit to cause the output timing of the voice guidance to correspond with the timing of shooting the image of said subject by varying a reproducing speed of said voice guidance based on at least one of the predicted ending time of inhalation and the predicted ending time of exhalation.

2. The image diagnosing apparatus according to claim 1, wherein:
   said voice output control unit causes the output timing of the voice guidance outputted from said voice guidance unit to correspond with the timing of shooting the image of said subject by controlling said voice guidance unit to match a starting time of shooting said subject with a time at which reproduction and outputting of said voice guidance end.

3. The image diagnosing apparatus according to claim 2, wherein:
   said voice output control unit exercises control over said voice guidance unit to cause a timing of breathing halt of said subject to correspond to the timing of shooting the image of said subject, which corresponds to the output timing of said voice guidance.

4. The image diagnosing apparatus according to claim 3, wherein:
   a respiration timing of said subject is a timing of sequentially performing one or more of inhalation, exhalation and breathing halt, and said voice output control unit exercises control over said voice guidance unit to cause a time at which reproduction and outputting of said voice guidance start to correspond with a timing of inhalation by said subject and to cause the time at which reproduction of said voice guidance ends to correspond with the timing of breathing halt by said subject.

5. The image diagnosing apparatus according to claim 1, wherein:
   said voice output control unit exercises control over said voice guidance unit to cause a timing of breathing halt of said subject to correspond to the timing of shooting the image of said subject, which corresponds to the output timing of said voice guidance.

6. The image diagnosing apparatus according to claim 5, wherein:
   a respiration timing of said subject is a timing of sequentially performing one or more of inhalation, exhalation and breathing halt, and said voice output control unit exercises control over said voice guidance unit to cause a time at which reproduction and outputting of said voice guidance start to correspond with a timing of inhalation by said subject and to cause a time at which reproduction of said voice guidance ends to correspond with the timing of breathing halt of said subject.

7. The image diagnosing apparatus according to claim 5, wherein:
   said voice guidance contains sequential notifications to said subject including one or more of the effects of "inhalation", "exhalation" and "breathing halt", and said voice output control unit exercises control over said voice guidance unit to cause a time at which the effect of "inhalation" of said voice guidance is reproduced to correspond with a timing of inhalation by said subject, to cause a time at which the effect of "exhalation" is reproduced to correspond with a timing of exhalation by said subject, and to cause a time at which the effect of "breathing halt" is reproduced to correspond with a timing of breathing halt by said subject.

8. The image diagnosing apparatus according to claim 5, further having:
a respiration sensor for measuring a respiration timing of said subject, said respiration sensor notifying said voice output control unit of the measured respiration timing of said subject.

9. The image diagnosing apparatus according to claim 8, wherein:
data for said voice guidance comprises a plurality of kinds of data classified by a pattern of the output timing of said voice guidance, and said voice output control unit exercises control over said voice guidance unit to cause the output timing of said voice guidance outputted from said voice guidance unit to correspond with the timing of shooting the image of said subject by using one kind of said classified plurality of kinds of data matched with the timing of shooting the image of said subject.

10. The image diagnosing apparatus according to claim 1, wherein:
data for said voice guidance comprises one kind of data, and said voice output control unit exercises control over said voice guidance unit to cause the output timing of the voice guidance outputted from said voice guidance unit to correspond with the timing of shooting the image of said subject by exercising control to adjust the reproducing speed and outputting said one kind of data to said voice guidance unit.

11. The image diagnosing apparatus according to claim 1, further comprising:
an input unit which allows inputting of a speed of reproduction and outputting to said voice guidance unit.

12. An image diagnosing method of shooting an image of a subject in an imaging space with an image diagnosing apparatus having a voice guidance unit which reproduces and outputs to the subject a prescribed voice guidance, the method comprising:
causing, using a voice output control unit configured to predict at least one of an ending time of inhalation by the subject and an ending time of exhalation by the subject, an output timing of the voice guidance outputted from said voice guidance unit to correspond with a timing of shooting the image of the subject by varying a reproducing speed of said voice guidance based on at least one of the predicted ending time of inhalation and the predicted ending time of exhalation.

13. The image diagnosing method according to claim 12, wherein:
causing an output timing of the voice guidance outputted from the voice guidance unit to correspond with a timing of shooting the image of the subject comprises matching a time at which the shooting of the subject starts with a time at which the reproduction and outputting of the voice guidance end.

14. The image diagnosing method according to claim 12 further comprising:
causing a timing of breathing halt of the subject to correspond with the output timing of the voice guidance, which corresponds with the timing of shooting the image of the subject.

15. The image diagnosing method according to claim 14, wherein a respiration timing of the subject is a timing of one or more in the sequential performance of inhalation, exhalation and breathing halt, the method further comprising:
causing a time at which reproduction and outputting of the voice guidance starts to correspond with a timing of inhalation by the subject; and
causing a time at which reproduction of the voice guidance ends to correspond with the timing of breathing halt by the subject.

16. The image diagnosing method according to claim 14, wherein the voice guidance contains sequential notifications to the subject including one or more of the effects of "inhalation", "exhalation" and "breathing halt", the method further comprising:
causing a time at which the effect of "inhalation" of the voice guidance is reproduced to correspond with a timing of inhalation by the subject;
causing a time at which the effect of "exhalation" is reproduced to correspond with a timing of exhalation by the subject; and
causing a time at which the effect of "breathing halt" is reproduced to correspond with a timing of breathing halt by the subject.

* * * * *